(12) United States Patent
Tsai et al.

(10) Patent No.: US 11,839,490 B2
(45) Date of Patent: Dec. 12, 2023

(54) THREE WAVELENGTH PULSE OXIMETRY

(71) Applicant: Garmin International, Inc., Olathe, KS (US)

(72) Inventors: Cheng-Yu Tsai, New Taipei (TW); Dong-Yi Wu, New Taipei (TW); Wei-Che Chang, New Taipei (TW)

(73) Assignee: Garmin International, Inc., Olathe, KS (US)

( * ) Notice: Subject to any disclaimer, the term of this patent is extended or adjusted under 35 U.S.C. 154(b) by 665 days.

(21) Appl. No.: 17/091,583

(22) Filed: Nov. 6, 2020

(65) Prior Publication Data

US 2022/0142569 A1    May 12, 2022

(51) Int. Cl.
*A61B 5/00*   (2006.01)
*A61B 5/083*  (2006.01)
*G04G 17/08*  (2006.01)

(52) U.S. Cl.
CPC ............ *A61B 5/681* (2013.01); *A61B 5/0833* (2013.01); *G04G 17/08* (2013.01); *A61B 2562/02* (2013.01)

(58) Field of Classification Search
CPC .... A61B 5/681; A61B 5/0833; A61B 5/14552
See application file for complete search history.

(56) References Cited

U.S. PATENT DOCUMENTS

| | | |
|---|---|---|
| 5,431,170 A | 7/1995 | Mathews |
| 5,524,617 A | 6/1996 | Mannheimer |
| 5,632,272 A | 5/1997 | Diab et al. |
| 9,292,008 B1 | 3/2016 | Ahamed et al. |
| 9,717,424 B2 | 8/2017 | Kulach |
| 10,215,698 B2 | 2/2019 | Han et al. |
| 10,912,469 B2 | 2/2021 | MacDonald et al. |
| 2003/0109775 A1 | 6/2003 | O'Neil et al. |
| 2011/0060200 A1 | 3/2011 | Bernreuter |
| 2012/0209095 A1 | 8/2012 | Huiku |

(Continued)

FOREIGN PATENT DOCUMENTS

| | | |
|---|---|---|
| EP | 3111834 A1 | 1/2017 |
| WO | 2015116891 A1 | 8/2015 |
| WO | 2017027551 A1 | 2/2017 |

OTHER PUBLICATIONS

Casson et al., Gyroscope vs. accelerometer measurements of motion from wrist PPG, during physical exercise, School of Electrical and Electronic Engineering, The University of Manchester, Manchester, UK, ICT Express 2, 2016, p. 175-179.

(Continued)

*Primary Examiner* — Tammie K Marlen
(74) *Attorney, Agent, or Firm* — Samuel M. Korte; Max M. Ali (57) ABSTRACT

An apparatus is disclosed for determining validity of a measured in-blood percentage of oxygenated hemoglobin. The apparatus has multiple pulse oximetry channels having at least three light sources of at least three distinct wavelengths, which are detected and converted to digital signals. The light sources are selectively activated, and two or more estimated in-blood percentages of oxygenated hemoglobin are calculated. It is determined whether a signal quality associated with the calculated in-blood percentages exceeds a predetermined accuracy threshold, and an associated validity indication is provided.

18 Claims, 6 Drawing Sheets

(56) References Cited

U.S. PATENT DOCUMENTS

| | | | |
|---|---|---|---|
| 2013/0030267 A1 | 1/2013 | Lisogurski et al. | |
| 2014/0213863 A1 | 7/2014 | Loseu et al. | |
| 2015/0065889 A1 | 3/2015 | Gandelman et al. | |
| 2015/0313549 A1 | 11/2015 | Lee et al. | |
| 2016/0287107 A1 | 10/2016 | Szabados et al. | |
| 2016/0296174 A1 | 10/2016 | Isikman et al. | |
| 2017/0105638 A1* | 4/2017 | Kulach | A61B 5/1118 |
| 2018/0028123 A1* | 2/2018 | Ahmed | A61B 5/002 |
| 2018/0116607 A1* | 5/2018 | Yu | A61B 5/02405 |
| 2018/0317785 A1 | 11/2018 | MacDonald et al. | |
| 2018/0317786 A1 | 11/2018 | Kulach et al. | |
| 2018/0317852 A1 | 11/2018 | MacDonald et al. | |
| 2020/0297226 A1 | 9/2020 | Lefrancois et al. | |

OTHER PUBLICATIONS

International Search Report and Written opinion from PCT/EP2018/061445 dated Aug. 16, 2018.
International Search Report and Written Opinion from PCT/EP2018/061446 dated Aug. 16, 2018.
International Search Report and Written Opinion from PCT/EP2019/061444 dated Aug. 16, 2018.
Nitzan et al., Pulse oximetry: fundamentals and technology update, Dove Press journal, Medical Devices: Evidence and Research Jul. 8, 2014.
Nogawa et al., Development of an optical arterial hematocrit measurement method: pulse hematometry. Engineering in Medicine and Biology 27th Annual Conference, Sep. 1-4, 2005.
Printout from https://www.apple.com/newsroom/2018/09/redesigned-apple-watch-series-4-revolutionizes-communication-fitness-and-health/ published prior to Mar. 16, 2020.
Printout from https://www.pcmag.com/reviews/apple-watch-series-4 published prior to Mar. 16, 2020.
U.S. Appl. No. 15/969,553, Kulach, filed May 2, 2018.
U.S. Appl. No. 15/969,574, MacDonald, filed May 2, 2018.
Wieben, O., Light Absorbance in Pulse Oximetry, published prior to Jan. 3, 2018.
Yadhuraj et al., Motion Artifact Reduction in Photoplethysmographic Signals: A Review, International Journal of Innovative Research & Development, Mar. 2013, vol. 2, Issue 3, p. 626-640.

* cited by examiner

THREE WAVELENGTH PULSE OXIMETRY

BACKGROUND

Pulse oximetry refers to processes for measuring and monitoring the percentage of oxygenated hemoglobin in blood. Arterial oxygen saturation (SaO2) is a medical parameter that provides a highly accurate measurement of oxygenated hemoglobin however, it requires access to arterial blood, the obtaining of which is typically painful and invasive. Measuring peripheral oxygen saturation (SpO2) through pulse oximetry, by contrast, is painless and non-invasive. Transmissive peripheral pulse oximetry involves transmitting two or more wavelengths of light through a peripheral part of the body, such as a foot, earlobe, or fingertip and measuring how much of the light is absorbed by pulsing arterial blood in peripheral capillaries. Typically, light sources of red and infrared or near-infrared wavelengths are selected because they are typically not absorbed by other non-vascular tissues and water that make up peripheral parts of the body. Reflective peripheral pulse oximetry involves reflecting two or more wavelengths of light through a peripheral part of the body and measuring a ratio of oxygenated hemoglobin absorption of the reflected light. Reflective peripheral pulse oximetry is convenient because reflective techniques can be employed at a surface of part of the body, such as the feet, forehead, chest, or wrist, in connection with a wearable device such as a smart watch. Unfortunately, reflective peripheral pulse oximetry tends to provide unstable readings resulting in difficulty in taking accurate, predictable, and repeatable readings. Accordingly, there is a need for more accurate and reliable reflective peripheral pulse oximetry technology and for systems to determine an associated level of validity of SpO2 measurements.

SUMMARY

Embodiments of the disclosure address the above-identified need by providing apparatuses for determining validity of a measured in-blood percentage of oxygenated hemoglobin. In particular, a first embodiment of the disclosure is broadly directed to an apparatus for determining validity of a measured in-blood percentage of oxygenated hemoglobin, the apparatus comprising: a first pulse oximetry channel comprising: a first light source producing light having a first wavelength and a first intensity, a second light source producing light having a second wavelength and a second intensity, a third light source producing light having a third wavelength and a third intensity, a first light detector configured to selectively detect light from the first pulse oximetry channel light sources, an analog to digital converter coupled with the first light detector, the analog to digital converter outputting a digital value corresponding to a measured intensity of light detected by the first light detector, a processor coupled with the display, the first pulse oximetry channel and the analog to digital converter, the processor programmed to execute steps comprising: selectively activating the first light source with a first activation intensity, receiving the first measured digital value corresponding to the intensity of light detected by the first light detector based on activation of the first light source, selectively activating the second light source with a second activation intensity, receiving the second measured digital value corresponding to the intensity of light detected by the first light detector based on activation of the second light source, calculating a first estimated in-blood percentage of oxygenated hemoglobin based on a comparison between the first and second digital values, selectively activating the third light source with a third activation intensity, receiving the third measured digital value corresponding to the intensity of light detected by the first light detector based on activation of the third light source, calculating a second estimated in-blood percentage of oxygenated hemoglobin based on a comparison between the second and third digital values, based on a comparison of the first and second estimated in-blood percentages of oxygenated hemoglobin, determining that a signal quality of the first estimated in-blood percentage of oxygenated hemoglobin exceeds a predetermined accuracy threshold, and based on the determination, providing a validity indication that the first estimated in-blood percentage is sufficiently accurate.

A second embodiment of the disclosure is broadly directed to an apparatus for determining validity of a measured in-blood percentage of oxygenated hemoglobin, the apparatus comprising: a first pulse oximetry channel comprising: a first light emitting diode producing light having a first wavelength and a first current, a second light emitting diode producing light having a second wavelength and a second current, a third light emitting diode producing light having a third wavelength and a third current, a first photodiode configured to selectively detect light from the first pulse oximetry channel light emitting diodes, an analog to digital converter coupled with the first light detector, the analog to digital converter outputting a digital value corresponding to a voltage derived from a measured intensity of light detected by the first light detector, a processor coupled with the display, the first pulse oximetry channel and the analog to digital converter, the processor programmed to execute steps comprising: selectively activating the first light emitting diode with a first activation current, receiving the first measured digital value corresponding to the intensity of light detected by the first light detector based on activation of the first light emitting diode, selectively activating the second light emitting diode with a second activation current, receiving the second measured digital value corresponding to the intensity of light detected by the first light detector based on activation of the second light emitting diode, calculating a first estimated in-blood percentage of oxygenated hemoglobin based on a comparison between the first and second digital values, selectively activating the third light emitting diode with a third activation current, receiving the third measured digital value corresponding to the intensity of light detected by the first light detector based on activation of the third light emitting diode, calculating a second estimated in-blood percentage of oxygenated hemoglobin based on a comparison between the second and third digital values, based on a comparison of the first and second estimated in-blood percentages of oxygenated hemoglobin, determining that a signal quality of the first estimated in-blood percentage of oxygenated hemoglobin exceeds a predetermined validity threshold, and based on the determination, providing an indication that the first estimated in-blood percentage is valid.

A third embodiment of the disclosure is broadly directed to an apparatus for determining validity of a measured in-blood percentage of oxygenated hemoglobin, the apparatus comprising: a first pulse oximetry channel comprising: a first light emitting diode producing light having a first wavelength and a first current, a second light emitting diode producing light having a second wavelength and a second current, a third light emitting diode producing light having a third wavelength and a third current, a first photodiode configured to selectively detect light from the first pulse oximetry channel light emitting diodes, a second pulse oximetry channel comprising: a fourth light source producing light having a fourth wavelength and a fourth intensity, a fifth light source producing light having a fifth wavelength and a fifth intensity; and a sixth light source producing light having a sixth wavelength and a sixth intensity, a second photodiode configured to selectively detect light from the second pulse oximetry channel light emitting diodes, an analog to digital converter coupled with the first light detector, the analog to digital converter outputting a digital value corresponding to a voltage derived from a measured intensity of light detected by the first light detector, a processor coupled with the display, the first pulse oximetry channel and the analog to digital converter, the processor programmed to execute steps comprising: selectively activating the first light emitting diode with a first activation current, receiving the first measured digital value corresponding to the intensity of light detected by the first light detector based on activation of the first light emitting diode, selectively activating the second light emitting diode with a second activation current, receiving the second measured digital value corresponding to the intensity of light detected by the first light detector based on activation of the second light emitting diode, calculating a first estimated in-blood percentage of oxygenated hemoglobin based on a comparison between the first and second digital values, selectively activating the third light emitting diode with a third activation current, receiving the third measured digital value corresponding to the intensity of light detected by the first light detector based on activation of the third light emitting diode, calculating a second estimated in-blood percentage of oxygenated hemoglobin based on a comparison between the second and third digital values, based on a comparison of the first and second estimated in-blood percentages of oxygenated hemoglobin, determining that a signal quality of the first estimated in-blood percentage of oxygenated hemoglobin exceeds a predetermined validity threshold, and based on the determination, providing an indication that the first estimated in-blood percentage is valid.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current disclosure will be apparent from the following detailed description of the embodiments and the accompanying drawing figures.

BRIEF DESCRIPTION OF THE DRAWING FIGURES

Embodiments of the disclosure are described in detail below with reference to the attached drawing figures, wherein.

The drawing figures do not limit the disclosure to the specific embodiments disclosed and described herein. The drawings are not necessarily to scale, emphasis instead being placed upon clearly illustrating the principles of the disclosure.

DETAILED DESCRIPTION

The disclosure describes various embodiments of a system for determining validity of a measured in-blood percentage of oxygenated hemoglobin using light sources having three or more wavelengths. The subject matter of embodiments of the disclosure is described in detail below to meet statutory requirements; however, the description itself is not intended to limit the scope of claims. Rather, the claimed subject matter might be embodied in other ways to include different steps or combinations of steps similar to the ones described in this document, in conjunction with other present or future technologies. Minor variations from the description below will be obvious to one skilled in the art and are intended to be captured within the scope of the claims. Terms should not be interpreted as implying any particular ordering of various steps described unless the order of individual steps is explicitly described.

The following detailed description of embodiments of the disclosure references the accompanying drawings that illustrate specific embodiments in which the disclosure can be practiced. The embodiments are intended to describe aspects of the disclosure in sufficient detail to enable those skilled in the art to practice the disclosure. Other embodiments can be utilized, and changes can be made without departing from the scope of the disclosure. The following detailed description is, therefore, not to be taken in a limiting sense. The scope of embodiments of the disclosure is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate reference to "one embodiment" "an embodiment", or "embodiments" in this description do not necessarily refer to the same embodiment and are also not mutually exclusive unless so stated and/or except as will be readily apparent to those skilled in the art from the description. For example, a feature, structure, or act described in one embodiment may also be included in other embodiments but is not necessarily included. Thus, the technology can include a variety of combinations and/or integrations of the embodiments described herein.

Figure 1:
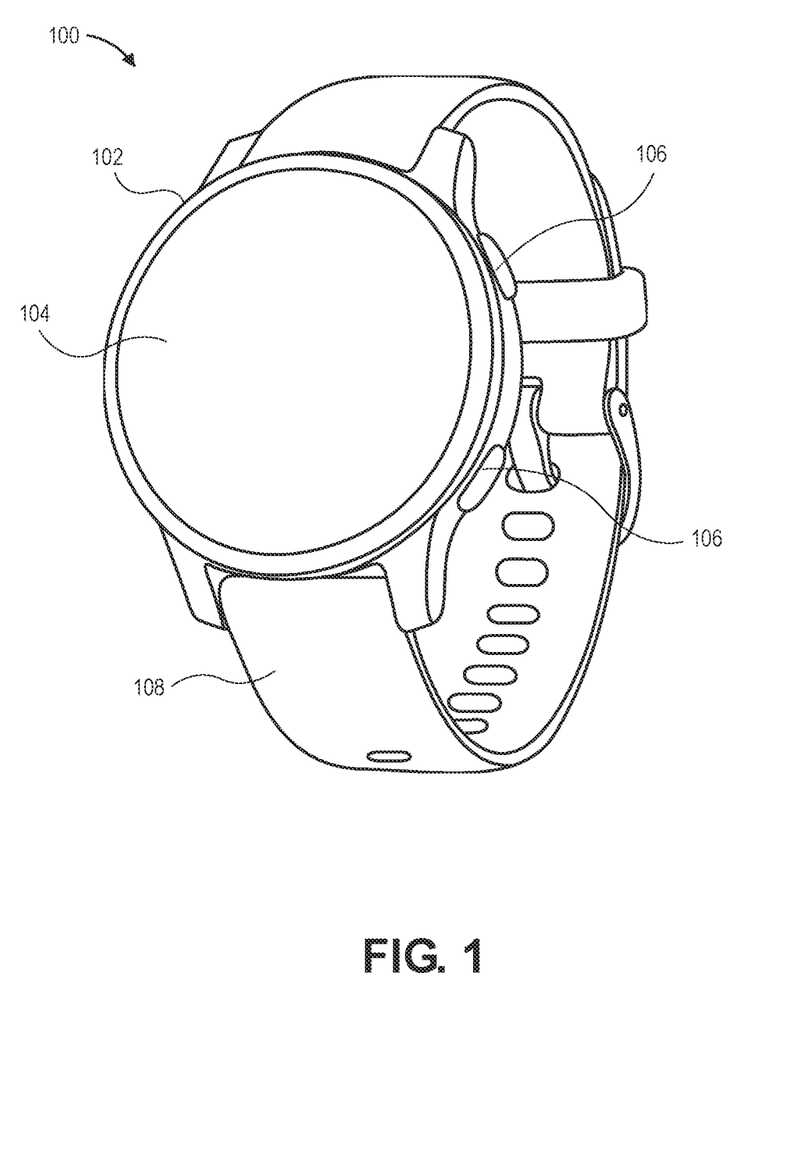
FIG. 1 depicts a view of one embodiment of a wearable device for performing three-wavelength pulse oximetry.

Turning first to FIG. 1, an exemplary a view of one embodiment of a wearable device for performing three-wavelength pulse oximetry is depicted. The device 100 may be configured in a variety of ways to determine and provide pulse oximetry information, as well as user-performance information and navigation functionality to the user of the device 100. The device 100 includes a housing 102 or a case configured to substantially enclose various components of the device 100. The housing 102 may be formed from a lightweight and impact-resistant material such as plastic, nylon, or combinations thereof, for example. The housing 102 may be formed from a conductive material, a non-conductive material, and combinations thereof. The housing 102 may include one or more gaskets, e.g., a seal, to make it substantially waterproof and/or water resistant. The housing 102 may include a location for a battery and/or another power source for powering one or more components of the device 100. The housing 102 may be a singular piece or may include multiple sections.

The device 100 includes a display device 104 with a user interface. The display device 104 may include a liquid crystal display (LCD), a thin film transistor (TFT), a light-emitting diode (LED), a light-emitting polymer (LEP), and/or a polymer light-emitting diode (PLED). The display device 104 may be capable of presenting text, graphical, and/or pictorial information. The display device 104 may be backlit such that it may be viewed in the dark or other low-light environments. One example embodiment of the display device 104 is a 100-pixel by 64-pixel film compensated super-twisted nematic display (FSTN) including a bright white light-emitting diode (LED) backlight. The display device 104 may include a transparent lens that covers and/or protects components of the device 100. The display device 104 may be provided with a touch screen to receive input (e.g., data, commands, etc.) from a user. For example, a user may operate the device 100 by touching the touch screen and/or by performing gestures on the screen. In some embodiments, the touch screen may be a capacitive touch screen, a resistive touch screen, an infrared touch screen, combinations thereof, and the like. The device 100 may further include one or more input/output (I/O) devices (e.g., a keypad, buttons, a wireless input device, a thumbwheel input device, etc.). The I/O devices may include one or more audio I/O devices, such as a microphone, speakers, and the like. Additionally, user input may be provided from movement of the housing 102, for example, an inertial sensor(s), e.g., accelerometer, may be used to identify vertical, horizontal, angular movement and/or tapping of the housing 102 or the lens.

In accordance with one or more embodiments of the present disclosure, the user interface may include one or more control buttons 106. As illustrated in FIG. 1, four control buttons 106 are associated with, e.g., adjacent, the housing 102. While FIG. 1 illustrates four control buttons 106 associated with the housing 102, it is understood that the device 100 may include a greater or lesser number of control buttons 106. In one embodiment, each control button 106 is configured to generally control a function of the device 100. Functions of the device 100 may be associated with a location determining component and/or a performance monitoring component as further described below in connection with FIG. 2B. Functions of the device 100 may include, but are not limited to, displaying a current geographic location of the device 100, mapping a location on the display 104, locating a desired location and displaying the desired location on the display 104, and presenting information based on a physiological characteristic (e.g., heart-rate, heart-rate variability, blood pressure, or SpO2 percentage, for example) or a physiological response (e.g., stress level, body energy level, etc.) of the individual.

Figure 2A:
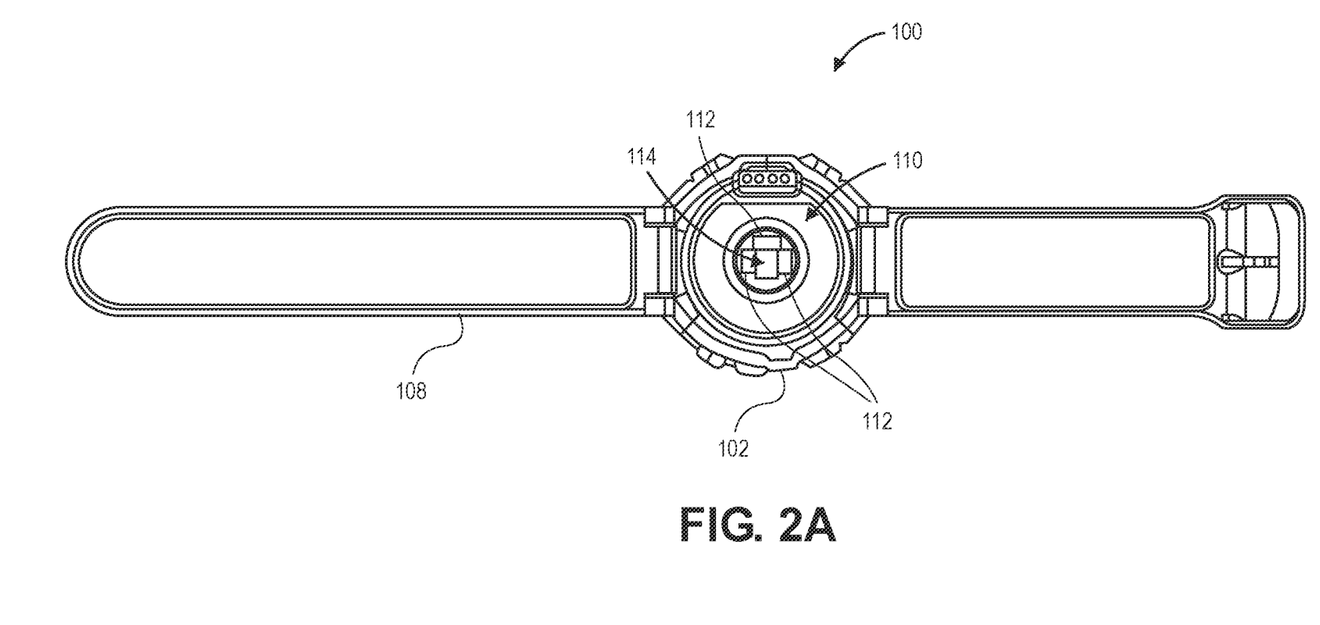
FIG. 2A depicts a bottom view of one embodiment of a wearable device for performing three-wavelength pulse oximetry.

FIG. 2A depicts a bottom view of one embodiment of a wearable device for performing three-wavelength pulse oximetry. The device 100 also includes a pulse oximetry signal assembly, including one or more emitters (e.g., LEDs 112) of visible and/or non-visible light and one or more receivers (e.g., photodiodes 114) of visible and/or non-visible light that generate a light intensity signal based on the received reflection of light.

The device 100 includes a means for attaching 108, e.g., a strap, that enables the device 100 to be worn by a user. In particular, when the device is worn by the user, one or more LEDs and one or more photodiodes may be securely placed against the skin of a user. The strap 108 is coupled to and/or integrated with the housing 102 and may be removably secured to the housing 102 via attachment of securing elements to corresponding connecting elements. Some examples of securing elements and/or connecting elements include, but are not limited to, hooks, latches, clamps, snaps, and the like. The strap 108 may be made of a lightweight and resilient thermoplastic elastomer and/or a fabric, for example, such that the strap 108 may encircle a portion of a user without discomfort while securing the device 100 to the user. The strap 108 may be configured to attach to various portions of a user, such as a user's leg, waist, wrist, forearm, upper arm, and/or torso.

Figure 2B:
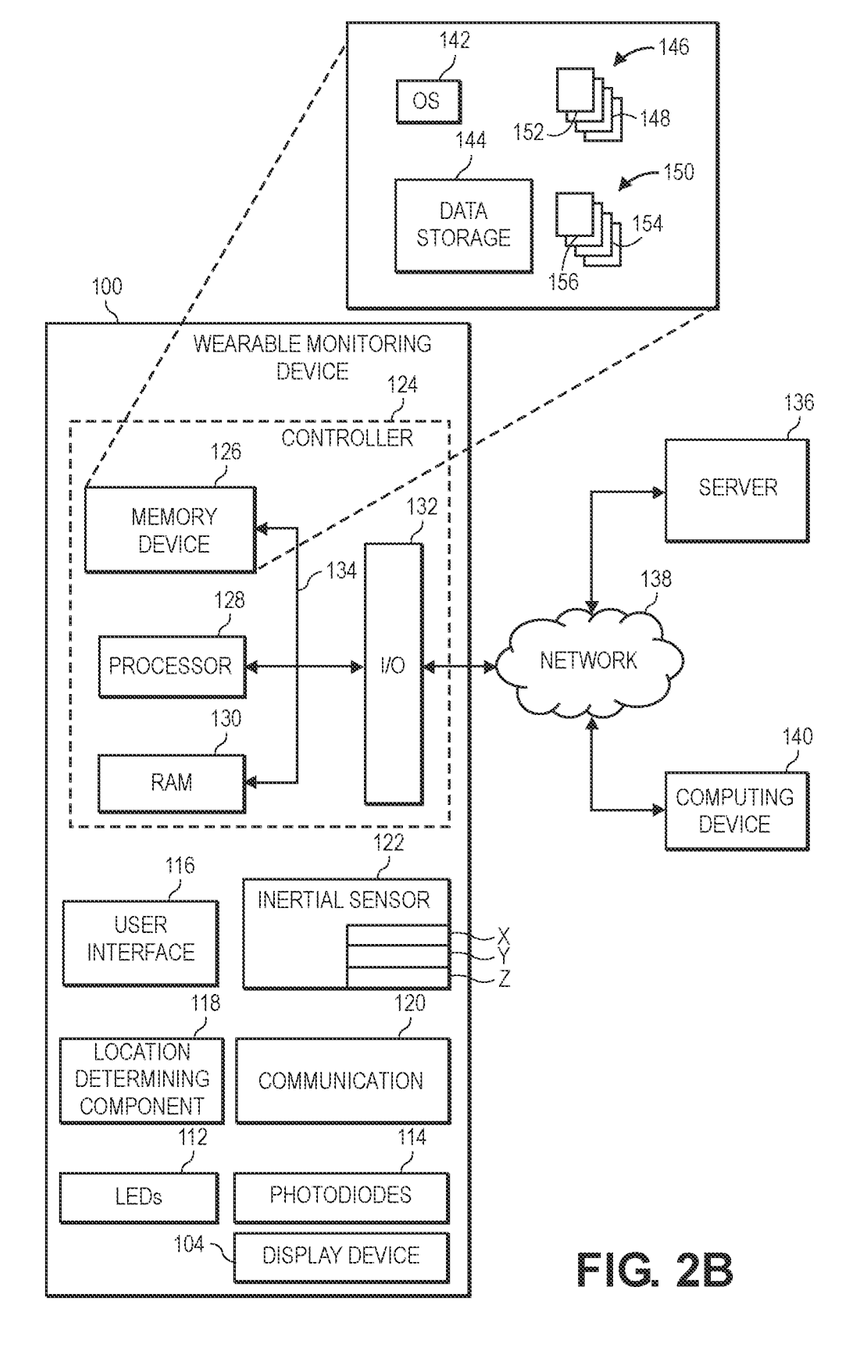
FIG. 2B depicts a system diagram showing the components of a system for carrying out embodiments of the disclosure.

FIG. 2B depicts a system diagram showing the components of a device 100 for carrying out embodiments of the disclosure. The device 100 includes a user interface module 116, a location determining component 118 (e.g., a global positioning system (GPS) receiver, assisted-GPS, etc.), a communication module 120, an inertial sensor 122 (e.g., accelerometer, gyroscope, etc.), and a controller 124. The device 100 may be a general-use wearable and mobile computing device (e.g., a watch, activity band, etc.), a cellular phone, a smartphone, a tablet computer, or a mobile personal computer, capable of monitoring a physiological characteristic and/or response of an individual as described herein. The device 100 may be a thin-client device or terminal that sends processing functions to a server device 136 via a network 138. Communication via the network 138 may include any combination of wired and wireless technology. For example, the network 138 may include a USB cable between the device 100 and a computing device 140 (e.g., smartphone, tablet, laptop, etc.) to facilitate the bi-directional transfer of data between the device 100 and the computing device 140.

The controller 124 may include a memory device 126, a microprocessor (MP) 128, a random-access memory (RAM) 130, and an input/output (I/O) circuitry 132, all of which may be communicatively interconnected via an address/data bus 134. Although the I/O circuitry 132 is depicted in FIG. 2B as a single block, the I/O circuitry 132 may include a number of different types of I/O circuits. The memory device 126 may include an operating system 142, a data storage device 144, a plurality of software applications 146, and/or a plurality of software routines 150. The operating system 142 of memory device 126 may include any of a plurality of mobile platforms, such as the iOS®, Android™, Palm® webOS, Windows® Mobile/Phone, BlackBerry® OS, or Symbian® OS mobile technology platforms, developed by Apple Inc., Google Inc., Palm Inc. (now Hewlett-Packard Company), Microsoft Corporation, Research in Motion (RIM), and Nokia, respectively. The data storage device 144 of memory device 126 may include application data for the plurality of applications 146, routine data for the plurality of routines 150, and other data necessary to interact with the server 136 through the network 138. In particular, the data storage device 144 may include cardiac component data associated with one or more individuals. The cardiac component data may include one or more compilations of recorded physiological characteristics of the user, including, but not limited to, a hemoglobin saturation values, a heart rate (HR), a heart-rate variability (HRV), a blood pressure, motion data, a determined distance traveled, a speed of movement, calculated calories burned, body temperature, and the like. In some embodiments, the controller 124 may also include or otherwise be operatively coupled for communication with other data storage mechanisms (e.g., one or more hard disk drives, optical storage drives, solid state storage devices, etc.) that may reside within the device 100 and/or operatively coupled to the network 138 and/or server device 136.

The device 100 also includes a pulse oximetry signal assembly including one or more light sources, such as LEDs 112. The pulse oximetry signal assembly also includes one or more light detectors such as photodiodes 114. In some embodiments, the LEDs 112 output visible and/or non-visible light and the one or more photodiodes 114 receive transmissions or reflections of the visible and/or non-visible light and convert the received light into electrical current, which, in some embodiments, is converted into a digital value by an analog to digital converter. Each LED 112 generates light based on an intensity determined by the processor. For example, LEDs 112 may include any combination of green light-emitting diodes (LEDs), red LEDs, and/or infrared or near-infrared LEDs that may be configured by the processor to emit light into the user's skin. In some embodiments, the red LEDs operate at a wavelength between approximately 610 and 700 nm. In some embodiments, a first LED produces light at approximately 630 nm, a second LED operates at approximately 940 nm, and a third LED operates at approximately 660 nm. The device 100 also includes display device 104 as described in connection with FIG. 1 above.

The device 100 also includes one or more photodiodes 114 capable of receiving transmissions or reflections of visible-light and/or infrared (IR) light output by the LEDs 112 into the user's skin and generating a SpO2 signal based on the intensity of the reflected light received by each photodiode 114. The light intensity signals generated by the one or more photodiodes 114 may be communicated to the processor. In embodiments, the processor includes an integrated a photometric front end for signal processing and digitization. In other embodiments, the processor is coupled with a photometric front end. The photometric front end may include filters for the light intensity signals and analog-to-digital converters to digitize the light intensity signals into SpO2 signals including a cardiac signal component associated with the user's heartbeat.

Typically, when the device 100 is worn against the user's body (e.g., wrist, fingertip, ear, etc.), the one or more LEDs 112 are positioned against the user's skin to emit light into the user's skin and the one or more photodiodes 344 are positioned near the LEDs 112 to receive light emitted by the one or more emitters after transmission through or reflection from the user's skin. The processor 128 of device 100 may receive a SpO2 signal based on a light intensity signal output by one or more photodiodes 114 based on an intensity of light after transmission of the light through or reflection from the user's skin that has been received by the photodiodes 114.

In both the transmitted and reflected uses, the intensity of measured light may be modulated by the cardiac cycle due to variation in tissue blood perfusion during the cardiac cycle. In activity environments, the intensity of measured light may also be strongly influenced by many other factors, including, but not limited to, static and/or variable ambient light intensity, body motion at measurement location, static and/or variable sensor pressure on the skin, motion of the sensor relative to the body at the measurement location, breathing, and/or light barriers (e.g., hair, opaque skin layers, sweat, etc.). Relative to these sources, the cardiac cycle component of the SpO2 signal can be very weak, for example, by one or more orders of magnitude.

The location determining component 118 generally determines a current geolocation of the device 100 and may process a first electronic signal, such as radio frequency (RF) electronic signals, from a global navigation satellite system (GNSS) such as the global positioning system (GPS) primarily used in the United States, the GLONASS system primarily used in the Soviet Union, or the Galileo system primarily used in Europe. The location determining component 118 may include satellite navigation receivers, processors, controllers, other computing devices, or combinations thereof, and memory. The location determining component 118 may be in electronic communication with an antenna (not shown) that may wirelessly receive an electronic signal from one or more of the previously-mentioned satellite systems and provide the first electronic signal to location determining component 118. The location determining component 118 may process the electronic signal, which includes data and information, from which geographic information such as the current geolocation is determined. The current geolocation may include geographic coordinates, such as the latitude and longitude, of the current geographic location of the device 100. The location determining component 118 may communicate the current geolocation to the processor 128. Generally, the location determining component 118 is capable of determining continuous position, velocity, time, and direction (heading) information.

In some embodiments, the inertial sensor 122 may incorporate one or more accelerometers positioned to determine the acceleration and direction of movement of the device 100. The accelerometer may determine magnitudes of acceleration in an X-axis, a Y-axis, and a Z-axis to measure the acceleration and direction of movement of the device 100 in each respective direction (or plane). It will be appreciated by those of ordinary skill in the art that a three-dimensional vector describing a movement of the device 100 through three-dimensional space can be established by combining the outputs of the X-axis, Y-axis, and Z-axis accelerometers using known methods. Single and multiple axis models of the inertial sensor 308 are capable of detecting magnitude and direction of acceleration as a vector quantity and may be used to sense orientation and/or coordinate acceleration of the user.

The SpO2 signal assembly (including LEDs 112 and photodiodes 114), location determining component 118, and the inertial sensor 122 may be referred to collectively as the "sensors" of the device 100. It is also to be appreciated that additional location determining components 118 and/or inertial sensor(s) 122 may be operatively coupled to the device 100. The device 100 may also include or be coupled to a microphone incorporated with the user interface module 116 and used to receive voice inputs from the user while the device 100 monitors a physiological characteristic and/or response of the user determines physiological information based on the cardiac signal.

Communication module 120 may enable device 100 to communicate with the computing device 140 and/or the server device 136 via any suitable wired or wireless communication protocol independently or using I/O circuitry 132. The wired or wireless network 138 may include a wireless telephony network (e.g., GSM, CDMA, LTE, etc.), one or more standard of the Institute of Electrical and Electronics Engineers (IEEE), such as 802.11 or 802.16 (Wi-Max) standards, Wi-Fi standards promulgated by the Wi-Fi Alliance, Bluetooth standards promulgated by the Bluetooth Special Interest Group, a near field communication standard (e.g., ISO/IEC 18092, standards provided by the NFC Forum, etc.), and so on. Wired communications are also contemplated such as through universal serial bus (USB), Ethernet, serial connections, and so forth.

The device 100 may be configured to communicate via one or more networks 138 with a cellular provider and an Internet provider to receive mobile phone service and various content, respectively. Content may represent a variety of different content, examples of which include, but are not limited to: map data, which may include route information; web pages; services; music; photographs; video; email service; instant messaging; device drivers; real-time and/or historical weather data; instruction updates; and so forth.

The user interface 116 of the device 100 may include a "soft" keyboard that is presented on the display device 104 of the device 100, an external hardware keyboard communicating via a wired or a wireless connection (e.g., a Bluetooth keyboard), and/or an external mouse, or any other suitable user-input device or component. As described earlier, the user interface 116 may also include or communicate with a microphone capable of receiving voice input from a vehicle operator as well as a display device 104 having a touch input.

With reference to the controller 124, it should be understood that controller 124 may include multiple microprocessors 128, multiple RAMs 130 and multiple memory devices 126. The controller 124 may implement the RAM 130 and the memory devices 126 as semiconductor memories, magnetically readable memories, and/or optically readable memories, for example. The one or more processors 128 may be adapted and configured to execute any of the plurality of software applications 146 and/or any of the plurality of software routines 150 residing in the memory device 126, in addition to other software applications. One of the plurality of applications 146 may be a client application 152 that may be implemented as a series of machine-readable instructions for performing the various functions associated with implementing the performance monitoring system as well as receiving information at, displaying information on, and transmitting information from the device 100. The client application 152 may function to implement a system wherein the front-end components communicate and cooperate with back-end components as described above. The client application 152 may include machine-readable instructions for implementing the user interface 116 to allow a user to input commands to, and receive information from, the device 100. One of the plurality of applications 146 may be a native web browser 148, such as Apple's Safari®, Google Android™ mobile web browser, Microsoft Internet Explorer® for Mobile, Opera Mobile™, that may be implemented as a series of machine-readable instructions for receiving, interpreting, and displaying web page information from the server device 136 or other back-end components while also receiving inputs from the device 100. Another application of the plurality of applications 146 may include an embedded web browser 148 that may be implemented as a series of machine-readable instructions for receiving, interpreting, and displaying web page information from the server device 136 or other back-end components within the client application 152.

The client applications 146 or routines 154 may include an accelerometer routine 154 that determines the acceleration and direction of movements of the device 100, which correlate to the acceleration, direction, and movement of the user. The accelerometer routine 154 may receive and process data from the inertial sensor 122 to determine one or more vectors describing the motion of the user for use with the client application 152. In some embodiments where the inertial sensor 122 includes an accelerometer having X-axis, Y-axis, and Z-axis accelerometers, the accelerometer routine 154 may combine the data from each accelerometer to establish the vectors describing the motion of the user through three-dimensional space. In some embodiments, the accelerometer routine 154 may use data pertaining to less than three axes.

The client applications 146 or routines 150 may further include a velocity routine 156 that coordinates with the location determining component 118 to determine or obtain velocity and direction information for use with one or more of the plurality of applications, such as the client application 152, or for use with other routines.

The user may also launch or initiate any other suitable user interface application (e.g., the native web browser 148, or any other one of the plurality of software applications 146) to access the server device 136 to implement the monitoring process. Additionally, the user may launch the client application 152 from the device 100 to access the server device 136 to implement the monitoring process.

After the above-described data has been gathered or determined by the sensors of the device 100 and stored in memory device 126, the device 100 may transmit information associated with measured blood oxygen saturation percentage (pulse oximetry signal), peak-to-peak interval (PPI), heart rate (HR), heart-rate variability (HRV), motion data (acceleration information), location information, stress intensity level, and body energy level of the user to computing device 140 and server device 136 for storage and additional processing. For example, in embodiments where the device 100 is a thin-client device, the computing device 140 or the server 136 may perform one or more processing functions remotely that may otherwise be performed by the device 100. In such embodiments, the computing device 140 or server 136 may include a number of software applications capable of receiving user information gathered by the sensors to be used in determining a physiological response (e.g., a stress level, an energy level, etc.) of the user. For example, the device 100 may gather information from its sensors as described herein, but instead of using the information locally, the device 100 may send the information to the computing device 140 or the server 136 for remote processing. The computing device 140 or the server 136 may perform the analysis of the gathered user information to determine a stress level or a body energy level of the user as described herein. The server 136 may also transmit information associated with the physiological response, such as a stress level, an energy level, of the user. For example, the information may be sent to computing device 140 or the server device 136 and include a request for analysis, where the information determined by the computing device 140 or the server device 136 is returned to device 100.

The disclosed techniques and described embodiments may be implemented in a wearable monitoring device having a housing implemented as a watch, a mobile phone, a hand-held portable computer, a tablet computer, a personal digital assistant, a multimedia device, a media player, a game device, or any combination thereof. The wearable monitoring device may include a processor configured for performing other activities.

Figures 3A, 3B, 3C:
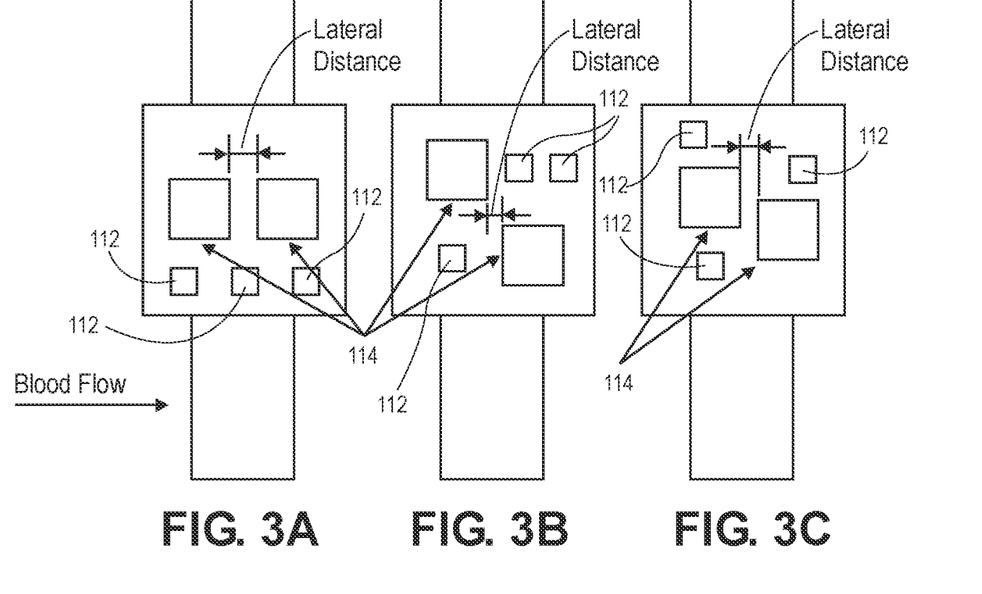
FIGS. 3A-3C depict various configurations for placement of photodiodes for carrying out embodiments of the disclosure.

FIGS. 3A-3C depict various configurations for placement of photodiodes for carrying out embodiments of the disclosure. In some embodiments, the wearable monitoring device includes a plurality of photodiodes 114 and a plurality of LEDs 112. FIGS. 3A-3C depict different configurations of two photodiodes 114 for positioning on a portion of a user's extremity or limb, such as the user's neck, lower arm, wrist, ankle, or torso. In accordance with the present disclosure, two or more photodiodes 114 are positioned on the user's skin tissue along an arterial path that is substantially parallel with a longitudinal axis of the user's extremity. The two photodiodes 114 are horizontally aligned and separated by a lateral distance that is substantially parallel with the longitudinal axis of the extremity, e.g., forearm, when the photodiodes 114 are attached to a user. Each photodiode 114 independently samples the adjacent skin tissue to detect a pulse wave as it travels from the heart to the end of the extremity. Although the two photodiodes 114 are horizontally positioned, the two photodiodes may be vertically offset with respect to each other, which may not adversely affect detection of the pulse wave as it travels along the limb and subsequent calculation of the physiological characteristic. That is, one photodiode 114 may be positioned closer to the ulna bone and the other photodiode 114 may be positioned closer to the radius bone (see FIGS. 3B and 3C), and vice-versa.

The wearable monitoring device includes at least one LED 112 positioned sufficiently near the two photodiodes 114 to enable the photodiodes 114 to operatively receive reflected light that was emitted from the at least one LED 112 and reflected from the user's skin tissue or transmitted through the user's soft tissue. In some embodiments, a plurality of LEDs 112 may be positioned around each and/or both photodiodes 114 such that the photodiodes 114 receive reflected or transmitted light emitted from the plurality of LEDs 112.

Figure 4:
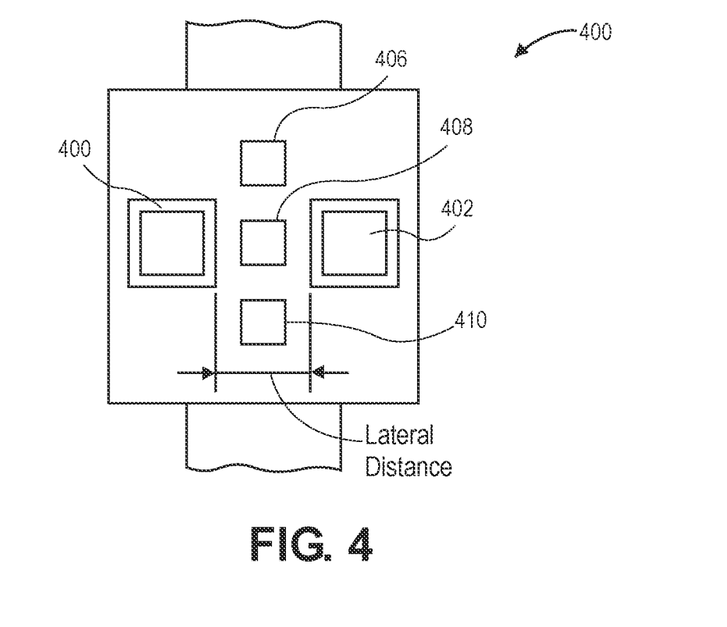
FIG. 4 depicts an exemplary placement of photodiodes and LEDs for carrying out embodiments of the disclosure.

FIG. 4 depicts an exemplary placement of photodiodes and LEDs for carrying out embodiments of the disclosure. In some embodiments, the wearable monitoring device may include two photodiodes 400, 402 aligned horizontally and a plurality of LEDs 406, 408, 410 vertically positioned between the two photodiodes 400, 402. The plurality of LEDs 406, 408, 410 may extend between the user's ulna and radius bones such that the light sensed by each photodiode 400, 402 is output by the LEDs 406, 408, 410. In another embodiment, the wearable monitoring device may include two or more photodiodes 400, 402 and a combination of one or more shared LEDs 406, 408, 410 positioned between the two photodiodes 400, 402 and producing light sensed by the two or more photodiodes 400, 402 and/or one or more unshared LEDs 406, 408, 410 that produce light that may be concentrated at the side of each photodiode 400 farther from the other photodiode 402.

When the two or more photodiodes 400, 406 are positioned close to each other, a higher sampling rate may be beneficial for each photodiode to generate the pulse oximetry signals to enable the processor to differentiate the peak of the pulse wave at the first photodiode 400 from the peak of the pulse wave at the second photodiode 406, which will occur shortly after the pulse wave passes by the first photodiode 400. At a sufficiently close distance, the second photodiode 406 may begin to detect (sense) the rise of the pulse wave before it has completely passed the first photodiode.

Figure 5:
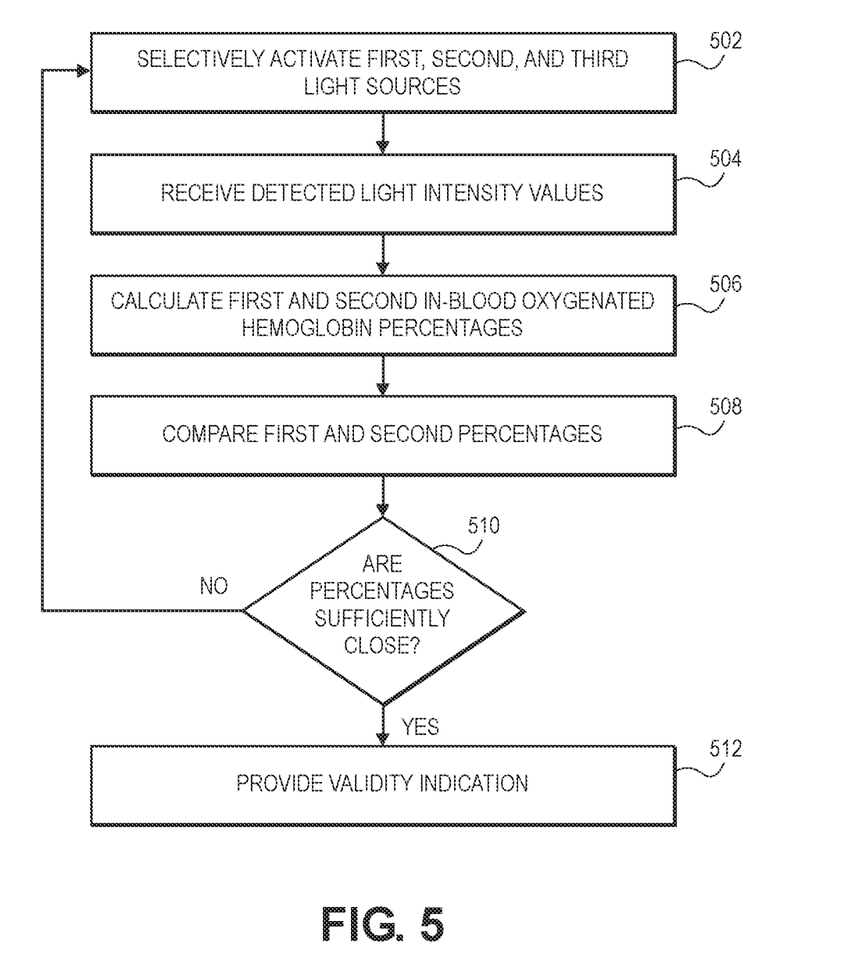
FIG. 5 depicts an exemplary process for determining validity of a measured in-blood percentage of oxygenated hemoglobin.

FIG. 5 depicts an exemplary process for determining validity of a measured in-blood percentage of oxygenated hemoglobin. The process begins at step 502 by selectively activating first, second, and third light sources. In some embodiments the first, second, and third light sources are LEDs. In one embodiment, the first light source is a red LED producing light having a wavelength of approximately 630 nm, the second light source is an infra-red LED producing light having a wavelength of approximately 940 nm, and the third light source is a red LED producing light having a wavelength of approximately 660 nm. In some embodiments, the range of wavelengths for the first LED varies from 620 nm to 640 nm. In other embodiments the range of wavelengths for the first LED varies from 610 nm to 650 nm. In some embodiments, the wavelength for the second LED is greater than 750 nm. In other embodiments the range of wavelengths for the second LED varies from 880 nm to 980 nm. In some embodiments the range of wavelengths for the third LED varies from 650 nm to 700 nm. In other embodiments the range of wavelengths for the first LED varies from 650 nm to 750 nm. In some embodiments, the light sources are selectively activated using a drive circuit that is selectively activated by a processor such as processor 128. In some embodiments, the light sources are selectively activated by the processor to produce light having a particular intensity based on an amount of activation current produced by the drive circuit.

In some embodiments, multiple channels of sets of light sources and light detectors are employed, operating independently. In some embodiments, a second channel is provided including fourth, fifth, and sixth light sources. In some embodiments, the second channel light sources are LEDs. In some embodiments, one or more additional light detectors, such as photodiodes are included to detect light from the fourth, fifth and sixth light sources. In various embodiments, the ranges of wavelengths employed are consistent with the wavelengths employed in a single channel. In some embodiments, wavelengths are within the same ranges, having different specific wavelength values between the first and second channels.

Next the process continues on to step 504 where the processor receives detected light intensity values. In some embodiments, the detected light intensity values are digital values obtained from an analog-to-digital converter that measures a digital value corresponding to current in a photodiode. The current in the photodiode is based on the intensity of light at a particular wavelength that is received at the photodiode. In some embodiments, at least three light sources are employed to generate light having three different wavelengths. In one embodiment, the first light source produces light having a wavelength of approximately 630 nm, the second light source produces light having a wavelength of approximately 940 nm, and the third light sources produces light having a wavelength of approximately 660 nm. In this embodiment, two different SpO2 values can be calculated, one by way of the ratio of the digital value corresponding to the intensity of 630 nm light to 940 nm light.

At step 506, first and second in-blood percentages of oxygenated hemoglobin percentages are calculated. For example, a first digital value is calculated by measuring a ratio of intensity of two different red lights to infrared light. In some embodiments, if two values are inconsistent, both values are removed from the samples. In some embodiments, measurements will result in accurate SpO2 calculations only when noise is absent from the subject measurement, i.e. when the wearable device is substantially motionless. In another embodiment, noise is subtracted to generate a more accurate measurement of SpO2. Given a range of noisy values, the noise is subtracted and if the two values are consistent, both measurements are determined to be accurate. In this embodiment, two alternative calculations may be performed. Because valid measurements taken with light sources of differing wavelength should generate the same value for SpO2, if the calculated results are sufficiently close, there is a high certainty that the measured SpO2 is valid. Accordingly, at step 508, the first and second percentages are compared. Next, at test 510 if the percentages are sufficiently close, a validity indication (step 512) is provided. If the percentages are not sufficiently close, the process continues back to step 502. In some embodiments, a SpO2 measurement is valid if a running root-mean-square deviation of the second percentage of oxygenated hemoglobin to the first percentage is within a sufficiently small deviation. In alternative embodiments, a SpO2 measurement is valid if the first and second percentages of oxygenated hemoglobin are within a sufficiently small absolute deviation of each other in a single measurement. The permitted deviation may be less than 1%, between 1-5%, between 5%-10%, more than 10%, more than 25%, or the like.

Figure 6A:
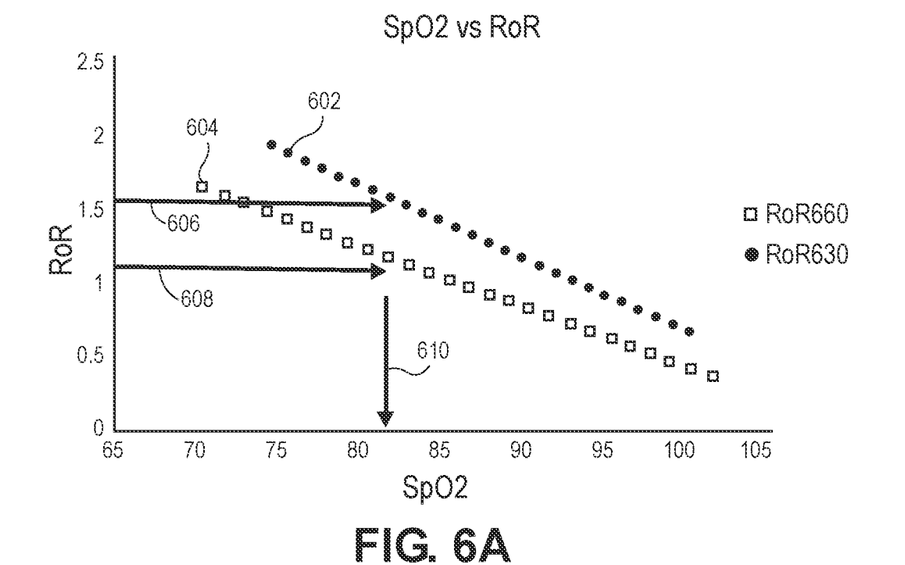
FIG. 6A depicts an exemplary graph confirming validity of a measured in-blood percentage of oxygenated hemoglobin.

FIG. 6A depicts an exemplary graph confirming validity of a measured in-blood percentage of oxygenated hemoglobin. Profile 602 corresponds to a ratio of ratios of the received 660 nm light as compared to the 940 nm light, and profile 604 corresponds to a ratio of ratios of the received 630 nm light as compared to the 940 nm light. In this example, ratios of ratios 606 and 608 correspond to measured intensities of each of the respective wavelengths and result in a consistent SpO2 calculation 610. Accordingly, in FIG. 6A a valid SpO2 calculation was performed.

Figure 6B:
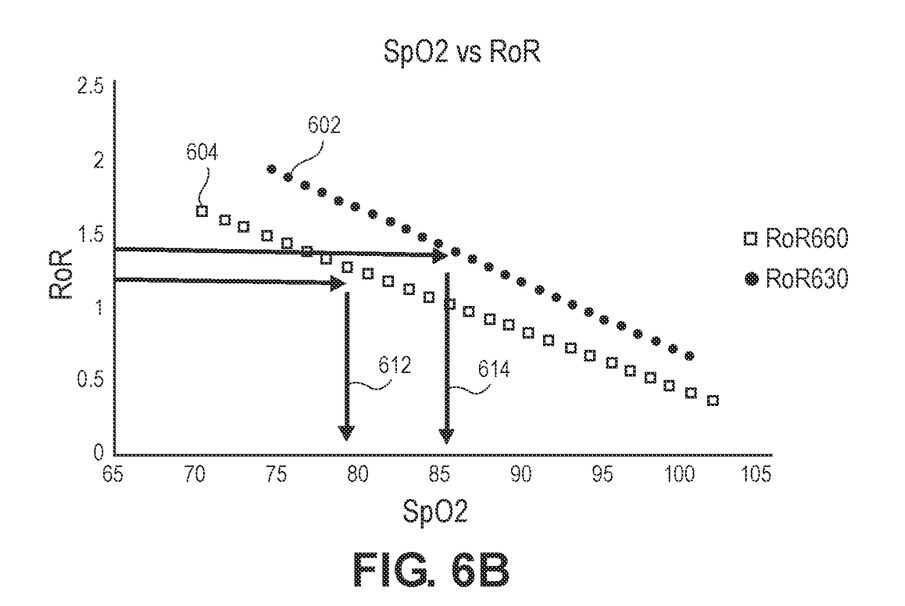
FIG. 6B depicts an exemplary graph indicating invalidity of a measured in-blood percentage of oxygenated hemoglobin.

FIG. 6B depicts an exemplary graph indicating invalidity of a measured in-blood percentage of oxygenated hemoglobin. In this figure, profile 602 corresponds to a ratio of ratios of the received 660 nm light as compared to the 940 nm light, and profile 604 corresponds to a ratio of ratios of the received 630 nm light as compared to the 940 nm light. In this example, ratios of ratios 606 and 608 correspond to measured intensities of each of the respective wavelengths and result in inconsistent SpO2 calculations 612 and 614. Accordingly, in FIG. 6B a valid SpO2 calculation was not performed.

Having thus described various embodiments, what is claimed as new and desired to be protected by Letters Patent includes the following:

1. An apparatus for determining validity of a measured in-blood percentage of oxygenated hemoglobin, the apparatus comprising:
a first pulse oximetry channel comprising:
a first light source configured to emit light having a first wavelength and a first intensity;
a second light source configured to emit light having a second wavelength and a second intensity;
a third light source configured to emit light having a third wavelength and a third intensity;
a first light detector configured to selectively detect reflections of light emitted by one or more light sources of the first pulse oximetry channel;
an analog to digital converter coupled with the first light detector, the analog to digital converter configured to generate and output a digital value corresponding to an intensity of light detected by the first light detector; and
a processor coupled with, the first pulse oximetry channel and the analog to digital converter, the processor configured to:
selectively activate the first light source to emit light having a first activation intensity;
receive from the analog to digital converter a first measured digital value corresponding to an intensity of light detected by the first light detector in response to activation of the first light source;
selectively activate the second light source to emit light having a second activation intensity;
receive from the analog to digital converter a second measured digital value corresponding to an intensity of light detected by the first light detector in response to activation of the second light source;
calculate a first estimated in-blood percentage of oxygenated hemoglobin based on a comparison between the first and second digital values;
selectively activate the third light source to emit light having a third activation intensity;
receive from the analog to digital converter a third measured digital value corresponding to an intensity of light detected by the first light detector in response to activation of the third light source;
calculate a second estimated in-blood percentage of oxygenated hemoglobin based on a comparison between the second and third digital values;
determine, based on a comparison of the first and second estimated in-blood percentages of oxygenated hemoglobin, whether a signal quality of the first estimated in-blood percentage of oxygenated hemoglobin exceeds a predetermined accuracy threshold; and
provide, based on the determination, a validity indication that the first estimated in-blood percentage is reliable.

2. The apparatus of claim 1, wherein the apparatus is a wearable device.

3. The apparatus of claim 1, wherein the first light source comprises a first light emitting diode, the second light source comprises a second light emitting diode, and the third light source comprises a third light emitting diode.

4. The apparatus of claim 3, wherein the first wavelength is between 610 nm and 650 nm, the second wavelength is greater than 750 nm, and the third wavelength is between 650 nm and 700 nm.

5. The apparatus of claim 1, wherein the light detector is a photodiode.

6. The apparatus of claim 1, further comprising a second pulse oximetry channel comprising:
a fourth light source configured to emit light having a fourth wavelength and a fourth intensity;
a fifth light source configured to emit light having a fifth wavelength and a fifth intensity; and
a sixth light source configured to emit light having a sixth wavelength and a sixth intensity.

7. The apparatus of claim 6, wherein the first light detector is further configured to selectively detect reflections of light emitted by one or more light sources of the second pulse oximetry channel.

8. The apparatus of claim 6, further comprising:
a second light detector configured to detect reflections of light emitted by one or more light sources of the second pulse oximetry channel light sources.

9. The apparatus of claim 1, further comprising a display coupled with the processor; wherein the processor is further configured to:
control the display to present the first estimated in-blood percentage of oxygenated hemoglobin.

10. An apparatus for determining validity of a measured in-blood percentage of oxygenated hemoglobin, the apparatus comprising:
a first pulse oximetry channel comprising:
a first light emitting diode configured to emit light having a first wavelength and a first electrical current;
a second light emitting diode configured to emit light having a second wavelength and a second electrical current;
a third light emitting diode configured to emit light having a third wavelength and a third electrical current;
a first photodiode configured to selectively detect reflections of light emitted by one or more light emitting diodes of the first pulse oximetry channel;
an analog to digital converter coupled with the first photodiode, the analog to digital converter configured to generate and output a digital value corresponding to a voltage derived from a measured intensity of light detected by the first photodiode; and
a processor coupled with the first pulse oximetry channel and the analog to digital converter, the processor configured to:
selectively activate the first light emitting diode to emit light associated with a first activation current;
receive from the analog to digital converter a first measured digital value corresponding to an intensity of light detected by the first photodiode in response to activation of the first light emitting diode;
selectively activate the second light emitting diode to emit light associated with a second activation current;
receive the second measured digital value corresponding to the intensity of light detected by the first photodiode based on activation of the second light emitting diode;
calculate a first estimated in-blood percentage of oxygenated hemoglobin based on a comparison between the first and second digital values;
selectively activate the third light emitting diode to emit light associated with a third activation current;
receive from the analog to digital converter a third measured digital value corresponding to an intensity of light detected by the first photodiode in response to activation of the third light emitting diode;
calculate a second estimated in-blood percentage of oxygenated hemoglobin based on a comparison between the second and third digital values;
determine, based on a comparison of the first and second estimated in-blood percentages of oxygenated hemoglobin, whether a signal quality of the first estimated in-blood percentage of oxygenated hemoglobin exceeds a predetermined validity threshold; and
provide, based on the determination, an indication that the first estimated in-blood percentage is valid.

11. The apparatus of claim 10, wherein the apparatus is a smart watch.

12. The apparatus of claim 10, wherein the first wavelength is between 610 nm and 650 nm, the second wavelength is greater than 750 nm, and the third wavelength is between 650 nm and 700 nm.

13. The apparatus of claim 10, further comprising a second pulse oximetry channel comprising:
a fourth light source configured to emit light having a fourth wavelength and a fourth electrical current;
a fifth light source configured to emit light having a fifth wavelength and a fifth electrical current; and
a sixth light source configured to emit light having a sixth wavelength and a sixth electrical current.

14. The apparatus of claim 13, wherein the first photodiode is further configured to selectively detect reflections of light emitted by one or more light emitting diodes of the second pulse oximetry channel.

15. The apparatus of claim 13, further comprising:
a second photodiode configured to detect reflections of light emitted by one or more light sources of the second pulse oximetry channel light emitting diodes.

16. An apparatus for determining validity of a measured in-blood percentage of oxygenated hemoglobin, the apparatus comprising:
a first pulse oximetry channel comprising:
a first light emitting diode configured to emit light having a first wavelength and a first current;
a second light emitting diode configured to emit light having a second wavelength and a second current;
a third light emitting diode configured to emit light having a third wavelength and a third current;
a first photodiode configured to selectively detect reflections of light emitted by one or more light emitting diodes of the first pulse oximetry channel;
a second pulse oximetry channel comprising:
a fourth light source configured to emit light having a fourth wavelength and a fourth current; and
a fifth light source configured to emit light having a fifth wavelength and a fifth current; and
a sixth light source configured to emit light having a sixth wavelength and a sixth current;
a second photodiode configured to selectively detect reflections of light emitted by one or more light emitting diodes of the second pulse oximetry channel;
an analog to digital converter coupled with the first photodiode and the second photodiode, the analog to digital converter configured to generate and output a digital value corresponding to a voltage derived from a measured intensity of light detected by the first photodiode and a digital value corresponding to a voltage derived from a measured intensity of light detected by the second photodiode; and
a processor coupled with the first pulse oximetry channel and the analog to digital converter, the processor configured to:
selectively activate the first light emitting diode to emit light associated with a first activation current;
receive from the analog to digital converter a first measured digital value corresponding to an intensity of light detected by the first photodiode in response to activation of the first light emitting diode;
selectively activate the second light emitting diode to emit light associated with a second activation current;
receive from the analog to digital converter a second measured digital value corresponding to an intensity of light detected by the first photodiode in response to activation of the second light emitting diode;
calculate a first estimated in-blood percentage of oxygenated hemoglobin based on a comparison between the first and second digital values;
selectively activate the third light emitting diode to emit light associated with a third activation current;
receive from the analog to digital converter a third measured digital value corresponding to an intensity of light detected by the first photodiode in response to activation of the third light emitting diode;

calculate a second estimated in-blood percentage of oxygenated hemoglobin based on a comparison between the second and third digital values;

determine, based on a comparison of the first and second estimated in-blood percentages of oxygenated hemoglobin, whether a signal quality of the first estimated in-blood percentage of oxygenated hemoglobin exceeds a predetermined validity threshold; and provide, based on the determination, an indication that the first estimated in-blood percentage is valid.

17. The apparatus of claim 16, wherein the first and fourth wavelengths are between 620 nm and 640 nm, the second and fifth wavelengths are between 880 nm and 980 nm, and the third and sixth wavelengths are between 650 nm and 700 nm.

18. The apparatus of claim 16, wherein the apparatus is a smart watch.

* * * * *